United States Patent [19]

Platt

[11] 4,263,144
[45] Apr. 21, 1981

[54] DEVICE FOR COLLECTING AND TRANSFERRING PARTICULATE MATERIAL

[75] Inventor: Steven G. Platt, El Sobrante, Calif.

[73] Assignee: The United States of America as represented by the Secretary of Agriculture, Washington, D.C.

[21] Appl. No.: 101,983

[22] Filed: Dec. 10, 1979

[51] Int. Cl.³ .............................................. B01D 15/08
[52] U.S. Cl. .................................. 210/658; 210/198.2; 422/70; 55/97; 55/417
[58] Field of Search .................... 55/391, 417, 468, 97; 210/31 C, 198 C, 191, 406; 422/70; 137/596, 625.29, 625.69

[56] References Cited

U.S. PATENT DOCUMENTS

| | | | |
|---|---|---|---|
| 1,945,820 | 2/1934 | Mitchell | 55/417 X |
| 2,300,765 | 11/1942 | Barnhart | 55/468 X |
| 2,532,614 | 12/1950 | Evans | 210/190 |
| 2,564,174 | 8/1951 | Roman | 210/406 X |
| 3,237,640 | 3/1966 | Whitlock et al. | 210/191 X |
| 4,029,487 | 6/1977 | Brandt | 55/417 X |

OTHER PUBLICATIONS

Simple Push-Pull Glass Valves by Platt et al., Journal of Chemical Education, p. 609, vol. 55, Sep. 1978.
Direct Transfer of Thin-Layer Chromatography into Vials by Preiss, Analytical Chemistry, vol. 49, No. 4, Apr. 1977, pp. 671 and 672.
Simple Device for Transferring and Eluting Thin-Layer Chromatographic Fractions by Sudilovsky et al., Analytical Biochemistry 45, 525–529, (1972).
Adaptation of Swinney Filter Holders for the Collection and Elution of Samples from Thin-Layer Plates by Nagle et al., J. Chromatog. 42 (1969), 121–123.
Technic for Separation and Solution of Zones in Thin-Layer Chromatography by Spikner et al., Chemist-Analyst, vol. 52, 1963, p. 50.
A Simple Device for Recovering Samples After Thin-Layer Chromatography by Levitt, Chromatography 4, 1971, pp. 75 and 76.
Preparative Thin-Layer Chromatography as an Alternative for Column Chromatography by Ritter et al., Nature, vol. 193, Mar. 10, 1962, pp. 941 and 942.
Chromatographic Identification of Complex Mixtures of High-Boiling Compounds by Janak, Nature, vol. 195, Aug. 18, 1962.

Primary Examiner—John Adee
Attorney, Agent, or Firm—M. Howard Silverstein; David G. McConnell; Theodore J. Leitereg

[57] ABSTRACT

A device and method are described for collecting and transferring particulate material. The device includes a housing with a porous member and means for connecting the housing to a vacuum attached thereto. A plunger, slidably mounted in the housing, opens and closes fluid-flow communication between the vacuum source and the porous member. In operation the porous member with a vacuum applied to one side thereof is contacted with first a porous filamentary filter and then with the particulate material. The particulate material detachably adheres to the filter and can be transferred to a collection area. The device and method of the invention are specifically suited for collecting and transferring adsorbent chromatographic fractions.

5 Claims, 4 Drawing Figures

DEVICE FOR COLLECTING AND TRANSFERRING PARTICULATE MATERIAL

BACKGROUND OF THE INVENTION

1. Field of the Invention

This invention relates to and has among its objects the provision of novel apparatus and methods for collecting and transferring particulate material. It is a particular object of the invention to rapidly and completely collect and transfer fractions of adsorbent chromatography material. Further objects of the invention will be evident from the following description wherein parts and percentages are by weight unless otherwise indicated.

2. Description of the Prior Art

Absorbent chromatography, for example, thin-layer chromatography has proven to be a useful technique for qualitatively and quantitatively separating small amounts of components of a mixture. Generally, a chromatographic adsorbent such as silica gel, alumina, cellulose, or the like, is adheringly applied to a support, e.g., a glass plate. The mixture to be separated is applied to one end of the adsorbentladen support, which end is then placed in a developing fluid generally an organic solvent or mixture of organic solvents appropriately selected to achieve sufficient separation of the components of the mixture. The developing fluid travels in an upwardly direction bringing along the components of the mixture. The rate of travel of the mixture of components is dependent upon their relative attractiveness to the adsorbent and the result is a separation of the components of the mixture. The location of the components on the adsorbent support can be determined by techniques well-known in the art. Once the separated components are located, the zones or fractions of chromatographic material containing a specific component are loosened from the support and transferred to a collection vessel. The problem is that cross contamination of the separated components occurs during the transferal and this cross-contamination reduces the effectiveness of the chromatographic separation.

Zone collectors for thin-layer chromatographic fractions are known in the art. Typical examples are described in:

Janak, J. (1962) *Nature* (London) 195, 696–697;
Ritter, F. J., and Meyer, G. M. (1962) *Nature* (London) 193, 941–942;
Goldrick, B., and Hirsch, J. (1963) *J. Lipid Res.* 4, 482–483;
Spikner, J. E., and Towne, J. C. (1963) *Chemist-Analyst* 52, 50;
Nagel, J. N., and Dittmer, J. C. (1969) *J. Chromatog.* 42, 121–123;
Levitt, M. J. (1971) *Chromatographia* 4, 75–76;
Sudilovsky, O., and Hinderaker, P. H. (1972) *Anal. Biochem.* 45, 525–529; and
Preiss, B. (1977) *Anal. Chem.* 49, 671–672.

The known collectors have one or more of the following disadvantages. First, a subsequently collected and transferred zone can be contaminated by adsorbent from a previous collection adhering to the collector. Second, porous members in the known devices often become clogged with adsorbent material. Third, the prior art apparatus require cleaning and drying after collection of one sample and before collection of another. Fourth, a separate device oftentimes is required for each fraction collected.

SUMMARY OF THE INVENTION

The invention described herein provides means for obviating the above-described problems. The device of the invention comprises a housing, with a means attached thereto for connecting the housing to a vacuum source. Also attached to the housing is a porous member. A plunger member is slidably mounted in the housing. The movement of the plunger member in the housing allows fluid-flow communication between the porous member and the vacuum source.

The method of the invention allows collection and transferal of particulate material, for example, a zone or fraction of adsorbent chromatographic material. A vacuum is applied to one side of a porous member and a porous filamentary filter is contacted with the other side of the porous member and held in place by the vacuum. The porous member is brought into contact with the particulate material in such a way as to cause the material to adhere to the porous filamentary filter. The material is transferred from the area in which it was collected and the vacuum is released thus disengaging the zone from the porous member.

The primary advantage of the invention is that adsorbent chromatographic fractions, for example, can be collected and transferred rapidly with negligible cross-contamination of different zones. A single apparatus of the invention can be used repeatedly without cleaning between collection of samples. In addition, clogging of the porous member is avoided.

DESCRIPTION OF THE PREFERRED EMBODIMENTS

The apparatus and method of the invention will be described in detail with reference to the attached drawings.

Figure 1:
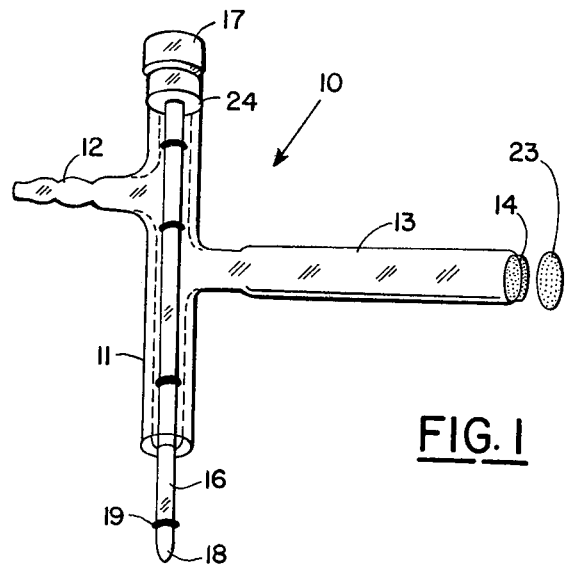
FIG. 1 is a three-dimensional view of the apparatus of the invention in a closed position.

FIG. 1 depicts collection and transferal device 10 with housing 11 fabricated from a material which is stable under reduced pressure. Thus, for example, 11 may be manufactured from glass, metal, rigid plastic, and the like. The material of choice is glass because of its light-weight and transparent properties. Housing 11 is open at both ends and has two appending members 12 and 13. Member 12 is designed for attachment to a vacuum source by conventional means. Member 13 is open at its end and fitted with porous member 14 such as a fritted glass disk, cheesecloth, or the like. Plunger member 15 is slidably mounted in housing 11 and comprises rod 16 with plunger cap member 17 and tip portion 18. Plunger member 15 generally is fabricated of glass, metal, rigid plastic, or the like. The diameter of rod 16 is less than the inside diameter of 11. O-rings 19-22, fabricated of resilient material, are attached to rod 16, preferably fitted into grooves in 16. The diameter of 19-22 is such as to provide non-fluid-flow seals between the O-rings and the inner wall 25 of 11. The placement of 19-22 on 11 is designed to yield an open configuration (FIG. 2) and a closed configuration (FIG.

1). When 10 is in an open configuration fluid-flow communication exists between 12 and 13. Thus, when 12 is attached to a vacuum source a vacuum is applied to the inside face of porous member 14. In a closed configuration fluid-flow communication no longer exists between 12 and 13, thus releasing the vacuum from the inside face of 14. Consequently, since 14 is porous, 13 gradually returns to atmospheric pressure. Cap member 17 has glass edge 24. Tip portion 18 has O-ring 19 which provides a physical stop point so rod 16 can't be pulled out of housing 11 when 10 is in an open configuration. The combination of plunger 15 and housing 11 is similar to push-pull valves described by Platt et al., *J. Chem. Educ.*, Vol. 55, page 609 (1978). Thus, in one respect the present device may be viewed as a push-pull valve with means for attachment to a vacuum source and an appending arm with a porous member at its end.

The diameter of appending member 13 and porous member 14 should be small enough to allow spot collection of the particulate material but large enough to minimize the number of collections necessary to remove all of a specific fraction of particulate material. Those skilled in the art will be able to determine the appropriate sizes based on the teachings contained herein.

Figure 2:
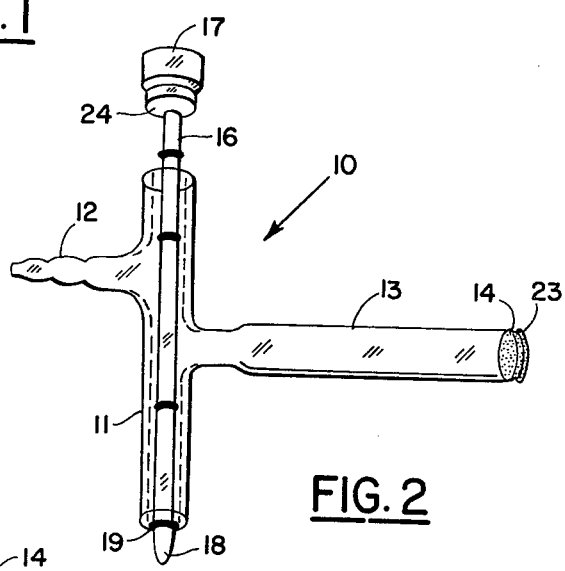
FIG. 2 is a three-dimensional view of the same apparatus in an open position.
Figure 3:
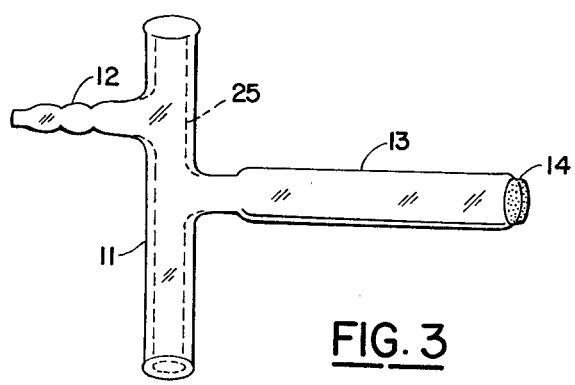
FIG. 3 is a three-dimensional view of the housing of the apparatus of the invention.
Figure 4:
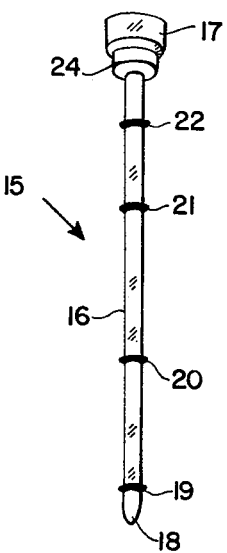
FIG. 4 is a three-dimensional view of the plunger member of the above apparatus.

The operation of the device and method of the invention is next described with reference to FIGS. 1 and 2. Reference to adsorbent chromatographic material is by way of example, not limitation. After identification, loosened fractions of adsorbent chromatographic material are formed according to conventional techniques such as by scraping the zone with a knife or the like to separate it from the plate and further aggregate it. Device 10 is attached to a vacuum source through member 12 and plunger 15 is pulled to place 10 in an open configuration. Porous filamentary filter 23, such as glassfiber filter paper or other similar material, with a diameter slightly greater than the diameter of 14 is attached to the outer face of 14 and held in position by means of the vacuum. The filter (23) covers 14 and extends past the edge of 14. The porous filter 23 has a thickness which, in conjunction with its porosity and the porosity of 14, allows facile fluid flow therethrough. The device, with 23 secured thereto, is next moved over the loosened and aggregated zone of adsorbent chromatographic material. The vacuum applied to the inside face of 14 causes the particles of chromatograhic material to adhere to the outside face of 23. When the zone has been collected on 23, the device is moved to an area where the collected material is to be deposited. At that point plunger 15 is moved to place the device in closed configuration. Since the vacuum is no longer being applied to the collected material, the zone and filter 23 fall free of 14. It should be understood that a number of collections of one zone may be required depending on the size of the zone and of 14 and 23.

To collect a different zone the above-described operation is repeated using a new filter 23. In this way facile collection and transference of adsorbent chromatographic fractions is obtained. Contamination between fractions is either negligible or avoided completely by the conjunctive use of porous member 14 and filter 23.

In the drawings and specification there has been set forth a preferred embodiment of the invention and, although specific terms are employed, they are used in generic and descriptive sense only and not for purposes of limitation. The scope of the invention is defined in the claims hereinbelow.

EXAMPLE

The invention is further demonstrated by the following illustrative example.

Glass thin layer chromatographic (tlc) plates precoated with silica gel and cellulose were used to determine recovery and cross-contamination with the collector. Aliquots (4–15 microliters) of radioactive sucrose in water (8159 disintegrations per minute per microliter, prepared from $^{14}CO_2$ by photosynthesis as described by Platt et al., *Plant Physiol.*, Vol. 60, pages 739–742 (1977) were spotted on the plates. When the spots were dry, the adsorbent areas containing the labeled sucrose were collected and transferred, using a device of the invention substantially as shown in FIGS. 1–4, to scintillation vials by the aforementioned procedure. Periodically, collection of adsorbent containing tracer was followed immediately by collection of a blank zone on the chromatographic plate to determine cross-contamination. After collection of the entire series of tlc zones, the samples were eluted by adding 5 ml of water to each vial and shaking them simultaneously in a water bath at 30° C. for 1.5 hours. This was followed by addition of 15 ml. of Aquasol 2 (New England Nuclear, Boston, Mass.), thorough shaking, and finally, scintillation counting. The counting efficiency, determined by adding a [$^{14}C$] toluene standard, was not significantly changed by the presence of the filter and adsorbent in the vials.

The results are summarized in the following table.

| TLC plate | Radioactivity applied (dpm) | Recovery[a] (%) | Blank[b] (dpm) |
|---|---|---|---|
| Cellulose, MN 300 | 32,636 | 100 | |
| 250-micrometer layer[c] | 122,385 | 100 | 39,43 |
| Cellulose, Avicel | 32,636 | 100 | |
| 250-micrometer layer[c] | 122,385 | 100 | 39,60 |
| Silica gel, Adsorbasil 5 | 32,636 | 98 | |
| 250-micrometer layer[d] | 122,385 | 98 | 44,41 |

[a]Three to six determinations (mean value)
[b]From each plate blank zones were collected immediately following two radioactive (122,385) zones. The values are essentially background values.
[c]Analtech, Newark, Delaware.
[d]Applied Science Laboratories, State College, Pennsylvania.

Having thus described the invention, what is claimed is:

1. A device for rapidly collecting and transferring a fraction of adsorbent chromatographic particulate material from a plurality of fractions obtained in thin-layer chromatography without cross contamination, which comprises in combination
   (a) a housing, open at both ends,
   (b) means affixed to said housing for connecting said housing to a vacuum source,
   (c) an appending member affixed to and having fluid-flow communication with said housing,
   (d) a porous member fitted into the non-affixed end of said appending member, the diameter of said appending member in (c) and said porous member being small enough to allow spot collection of a fraction of adsorbent chromatographic particulate material from a plurality of fractions obtained in thin-layer chromatography without cross contamination but large enough to minimize the number of collections necessary to collect and transfer all of said fraction,
   (e) a plunger member slidably mounted in said housing, the slidable movement of which alternately opens and closes fluid-flow communication between the vacuum source and said porous member, and (f) a porous filamentary filter having a diameter slightly greater than said porous member and detachably adhering to said porous member by means of said vacuum.

2. The device of claim 1 wherein the combination of said plunger in said housing is a push-pull valve.

3. The device of claim 1 which further includes O-rings mounted on said plunger to provide non-fluid-flow seals between said O-rings and said housing.

4. The device of claim 1 wherein said porous member is a fritted glass disk.

5. A method for rapidly collecting and transferring one fraction of adsorbent chromatographic particulate material from a plurality of fractions obtained in thin-layer chromatography without cross contamination, which comprises the steps of (a) applying a vacuum to one side of a porous member, (b) contacting the other side of the porous member with a porous filamentory filter causing the filter to adhere to the porous member, (c) contacting the porous filamentary filter adhering to the porous member with a fraction of adsorbent chromatographic particulate material in a plurality of fractions obtained in thin-layer chromatography, causing the material to adhere to the porous filamentary filter, (d) transferring the porous filamentary filter with the fraction of particulate material adhering thereto, and (e) releasing the vacuum causing the fraction of particular material and the porous filamentary filter to be disengaged.

* * * * *